US005964591A

United States Patent [19]
Beaty et al.

[11] Patent Number: 5,964,591
[45] Date of Patent: Oct. 12, 1999

[54] IMPLANT DELIVERY SYSTEM

[75] Inventors: Keith D. Beaty, Jupiter; Richard J. Lazzara, Lake Worth; Daniel J. Tarullo, Jupiter, all of Fla.; Thomas S. Heylmun, Meriden, Conn.

[73] Assignee: Implant Innovations, Inc., Palm Beach Gardens, Fla.

[21] Appl. No.: 09/057,087

[22] Filed: Apr. 8, 1998

Related U.S. Application Data

[60] Provisional application No. 60/043,131, Apr. 9, 1997.

[51] Int. Cl.⁶ .................................................. A61C 8/00
[52] U.S. Cl. ........................ 433/173; 433/141; 433/214; 433/215
[58] Field of Search ........................... 433/141, 172–176, 433/214, 215; 206/63.5, 339; 81/436

[56] References Cited

U.S. PATENT DOCUMENTS

| | | | |
|---|---|---|---|
| 4,011,602 | 3/1977 | Rybicki et al. | 433/173 |
| 4,444,310 | 4/1984 | Odell | 206/366 |
| 4,490,116 | 12/1984 | Deutsch et al. | 433/215 |
| 4,671,410 | 6/1987 | Hansson et al. | 206/438 |
| 4,712,681 | 12/1987 | Branemark et al. | 206/438 |
| 4,722,733 | 2/1988 | Howson | 604/411 |
| 4,744,754 | 5/1988 | Ross | 433/173 |
| 4,763,788 | 8/1988 | Jorneus et al. | 206/438 |
| 4,824,372 | 4/1989 | Jorneus et al. | 433/174 |
| 4,856,648 | 8/1989 | Krueger | 206/63.5 |
| 4,856,994 | 8/1989 | Lazzara et al. | 433/173 |
| 4,865,648 | 9/1989 | Krueger | 206/63.5 |
| 4,955,811 | 9/1990 | Lazzara et al. | 433/173 |
| 4,978,007 | 12/1990 | Jacobs et al. | 206/469 |
| 5,026,285 | 6/1991 | Durr et al. | 433/173 |
| 5,049,072 | 9/1991 | Lueschen | 433/173 |
| 5,049,073 | 9/1991 | Lauks | 433/173 |
| 5,062,800 | 11/1991 | Niznick | 433/229 |
| 5,069,622 | 12/1991 | Rangert et al. | 433/173 |
| 5,100,323 | 3/1992 | Friedman et al. | 433/173 |
| 5,105,690 | 4/1992 | Lazzara et al. | 81/436 |
| 5,106,300 | 4/1992 | Voitik | 433/173 |

(List continued on next page.)

FOREIGN PATENT DOCUMENTS

| | | |
|---|---|---|
| 2230615 | 2/1996 | Canada . |
| 0 231 730 | 8/1987 | European Pat. Off. . |
| 0 727 193 A1 | 2/1996 | European Pat. Off. . |
| 2 635 455 | 8/1990 | France . |
| 40 28 855 | 3/1992 | Germany . |
| WO 97/06930 | 2/1997 | WIPO . |
| WO 97/24977 | 7/1997 | WIPO . |
| WO 97/28755 | 8/1997 | WIPO . |
| WO 98/55039 | 12/1998 | WIPO . |

OTHER PUBLICATIONS

Calcitek, *Communique*, vol. 1, No. 2, 6 pages, believed to be one year before filing date.

(List continued on next page.)

*Primary Examiner*—John J. Wilson
*Assistant Examiner*—Patrick A. Hilsmier
*Attorney, Agent, or Firm*—Arnold White & Durkee

[57] ABSTRACT

A set of components are set forth which efficiently deliver a dental implant to a site at which the implant is to be installed in living jawbone. The implant has a gingival end with a manipulating fitting and a threaded bore extending inwardly from the gingival end. The set of components include a carrier device having an upper end, a lower end, a through-bore extending between the lower and upper ends, and a fitting for mating with the manipulating fitting of the implant. The through-bore in the region adjacent to the upper end includes a non-circular socket for receiving an implant-insertion tool that imparts movement to the carrier device and the implant. The set of components further includes a screw for attaching said carrier device to said implant. The screw has a lower threaded portion for engaging the threaded bore of the implant and a head for stopping on a shoulder within the through-bore of the carrier device. The set may further include an impression coping which attaches to the carrier and allows the clinician to take an impression of the site immediately after installing the implant.

47 Claims, 11 Drawing Sheets

U.S. PATENT DOCUMENTS

| | | | |
|---|---|---|---|
| 5,125,840 | 6/1992 | Durr et al. | 433/173 |
| 5,135,395 | 8/1992 | Marlin | 433/174 |
| 5,140,877 | 8/1992 | Sloan | 81/439 |
| 5,145,371 | 9/1992 | Jorneus | 433/173 |
| 5,158,458 | 10/1992 | Perry | 433/141 |
| 5,180,303 | 1/1993 | Hornburg et al. | 433/173 |
| 5,312,254 | 5/1994 | Rosenlicht | 433/173 |
| 5,322,443 | 6/1994 | Beaty | 433/141 |
| 5,344,457 | 9/1994 | Pilliar et al. | 623/16 |
| 5,368,160 | 11/1994 | Leuschen et al. | 206/339 |
| 5,437,550 | 8/1995 | Beaty et al. | 433/141 |
| 5,462,436 | 10/1995 | Deaty | 433/141 |
| 5,489,210 | 2/1996 | Hanosh | 433/173 |
| 5,538,428 | 7/1996 | Staubli | 433/173 |
| 5,564,924 | 10/1996 | Kwan | 433/173 |
| 5,582,299 | 12/1996 | Lazzara et al. | 206/63.5 |
| 5,591,029 | 1/1997 | Zuest | 433/173 |
| 5,626,227 | 5/1997 | Wagner et al. | 206/369 |
| 5,685,715 | 11/1997 | Beaty et al. | 433/173 |
| 5,692,904 | 12/1997 | Beaty et al. | 433/141 |

OTHER PUBLICATIONS

Dentsply, "Paragon Implant Surgical System," 20 pages (Sep.1996).

Dentsply, "Product Catalog," 21 pages (1992).

Dentsply, "Surgical Manual," 18 pages (1993).

Implamed Product Catalog, 40 pages (1995).

"Implant Dentistry Techniques: Beginning the Restorative Process at the Time of Surgery with the Immediate Impression Implant System from Setri–Oss," *Dental Products Report*, 2 pages (1996).

Implant Innovatins, "3i Unisystem™: A Unified Implant Delivery System," 6 pages, believed to be one year before filing date.

Implant Innovations, "Osseotite Technology Report," 11 pages (Jan.1997).

Implant Innovations, "Surgical Catalog," 54 pages, Lit #CATSU, believed to be one year before filing date.

Implant Innovations, "Surgical Manual," 34 pages (1992).

Implant Innovations, "Surgical Manual," 67 pages, (Jan.1994).

Implant Support Systems, Inc., "Catalog," 42 pages (1993).

Imtec, "Surgical and Prosthetic Catalog," 5th edition 14 pages (1995).

Lifecore Biomedical, "Product Catalog," 5 pages (1995).

Nobelpharma, "Smiline: Prosthetics Product Catalog," 24 pages (1991).

Park Dental Research Corp., "Star/Vent™: Osseointegrated Screw Implant Technique," 5 pages (1990).

Steri–Oss Dental Implants, "Immediate Impression Implant System," 4 pages (1996).

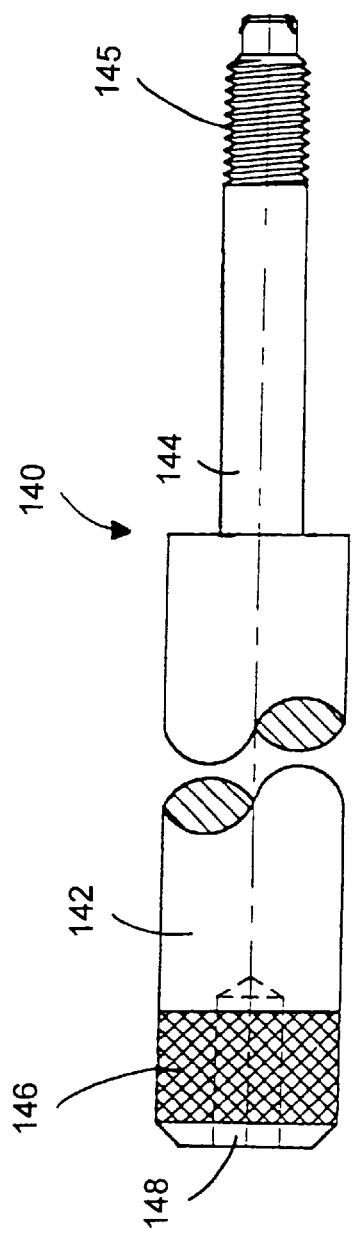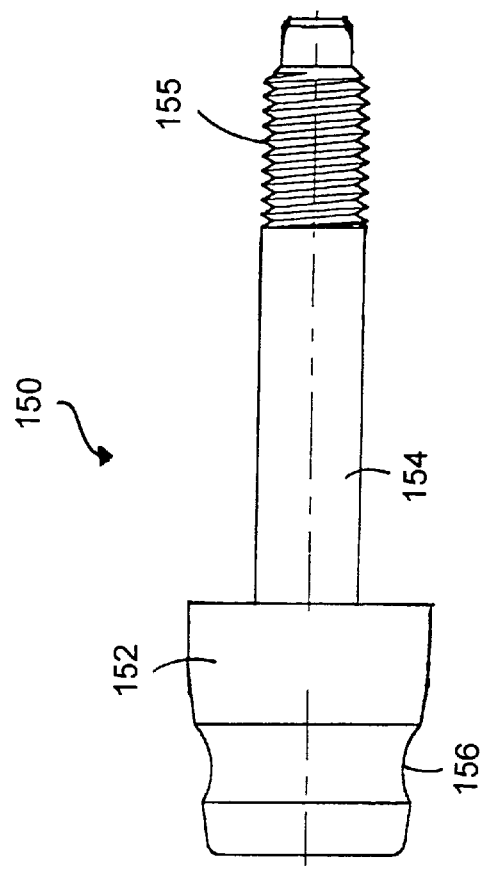

IMPLANT DELIVERY SYSTEM

This appln. claims the benefit of U.S. Provisional Appln. No. 60/043,131 filed Apr. 9, 1997.

FIELD OF THE INVENTION

The invention relates to a system and a technique for delivering and installing an implant in living bone. Specifically, the system includes an implant and a carrier attached thereto that are packaged together and delivered to the installation site within the living bone. The system also includes a variety of tools that provide flexibility in the installation process and additional components that permit the taking of impressions during first-stage surgery.

BACKGROUND OF THE INVENTION

It is known to enclose sterilized dental implants in packages that will preserve sterility until opened. The packages are delivered to the clinician who elects when and where to open the package. It is also known to include in such packages carrier devices attached to the implants enabling the implant to be manipulated without directly touching it.

Placing a dental implant in the jawbone of a patient is typically the beginning of several procedures which have been developed for providing implant-supported dentition. All procedures use components, frequently referred to as an "impression coping," for transferring to the dental laboratory information about the patient's mouth in the area of the implant on which the dentition is to be supported. Until fairly recently, it has been the usual practice to delay this information-transfer step several months after installing the implant to allow the implant to "osseointegrate" with the host bone. The result is a two-stage surgical procedure; the first-stage includes the installation of the implant; the second stage involves another surgery in which the gum tissue is reopened and an impression coping is fitted to the implant to gather the needed information. Since laboratory procedures cannot begin without this information, the development of a patient's dental prosthesis was generally delayed about 3 to 6 months while the osseointegration process occurred.

Generally, the carrier has a non-rotational engagement surface (i.e. non-circular) that a dental tool engages. When the implant has external threads, the dental tool is rotated such that the rotation imparted on the combination of the carrier and the implant screws the implant into the jawbone. In some situations, however, it is necessary to have a longer carrier because the gingiva above the jawbone is thick such that only a smaller portion of the carrier is exposed through the gingiva. In that situation, clinicians often remove the standard carrier from the implant and install onto the implant a longer carrier to accommodate the thicker gingiva. However, any time the clinician touches the implant, there is a risk that the sterile surfaces on the implant may become contaminated.

Recently, a protocol was developed which includes the taking of an impression of the patient's mouth during first-stage surgery. Immediately after the implant has been installed into its final position at the site of the jawbone, the clinician removes the carrier from the implant and installs onto the implant an impression coping. Once the impression coping is installed on the implant, the clinician then applies impression material to the region to take the impression of the site in the patient's mouth. The impression would then allow for the development of a temporary, or possibly, a permanent dentition that would be attached to the implant after osseointegration. One of the problems associated with this new protocol is the potential for movement of the implant, which has been accurately placed into the patient's jawbone, caused by the attachment of the impression coping.

SUMMARY OF THE INVENTION

The present invention provides for an implant delivery system that includes an implant, a carrier, and an implant screw attaching the implant to the carrier. The implant can be of a variety of types and typically includes an internally-threaded bore extending along its central axis. The carrier has a through-bore extending entirely therethrough in which the implant screw resides. The implant screw connects the implant to the carrier such that the lower surface of the carrier abuts the upper surface of the implant. A pair of non-circular fittings on the implant and carrier lock these two components against rotation relative to one another.

The through-bore of the carrier includes a non-circular socket that is to be engaged by a correspondingly shaped section of a coupling tool. The coupling tool is engaged by a device which imparts movement on the combination of the implant and the carrier that is necessary to install the implant into its final position within the jawbone. When the implant includes an externally threaded body, the device may be a dental hand piece that imparts rotational movement on the implant to screw it into the bone. The coupling tool can be made in a variety of lengths such that the clinician selects the appropriate length for the prevailing conditions in the patient's mouth.

After the implant is installed in its final position, the carrier is removed through the use of a driver. The driver includes a surface which the clinician grasps, a shank extending from the grasping surface, and a guide that is connected to the shank. The guide is free to move rotationally around the shank, but is limited in its axial movement along the shank. The lower end of the shank includes a surface which is non-rotationally coupled to the implant screw. The guide includes at its lower end an engaging portion which is to be non-rotationally engaged within the socket of the carrier. During removal of the implant screw, the engaging portion of the guide is coupled to the internal socket of the carrier and the lower end of the shank is engaged within a driver socket in the implant screw. When the clinician rotates the grasping surface, the carrier is held steady on the implant while the implant screw is rotated such that it releases the carrier from the implant. Due to the configuration of the driver, the carrier can be removed from the implant without imparting any motion whatsoever on the carrier and, therefore, the implant.

If the clinician so desires, he or she can also utilize the combination of the implant and the carrier to take an impression of the patient's mouth during first-stage surgery. An impression coping and its associated bolt can be affixed into the socket of the carrier. The impression coping has at its lower end an expandable non-rotational boss that fits within the carrier's socket. When the bolt is threaded into an internally threaded bore within the impression coping, the boss expands outwardly such that it becomes press fit into the socket of the carrier. This press fit engagement provides enough retention force so that an impression can be made by the clinician without the risk of the impression coping loosening from the carrier.

The bolt associated with the impression components can include an elongated head so that the bolt and impression component act as a "pick-up" type impression coping. Alternatively, a short-headed bolt can be used so that the bolt and impression component act as a "transfer" type impression coping. In either case, after the impression is taken, the carrier is reattached to the impression coping using the bolt. The combination of the carrier and impression coping is then used with the impression material in the dental laboratory to develop a prosthetic tooth for the patient.

Regardless of whether the clinician chooses to take an impression of the region during first-stage surgery, he or she must cover the internally threaded bore of the implant after the carrier is removed. Thus, the combination of the implant carrier and implant screw is typically packaged with a healing cap. The healing cap mates with the internally threaded bore of the implant and is placed thereon prior to suturing the gingiva.

BRIEF DESCRIPTION OF THE DRAWINGS

FIG. 9 illustrates a pick-up bolt used with the impression coping of FIG. 8;

FIG. 10 illustrates a transfer bolt used with the impression coping of FIG. 8.

DETAILED DESCRIPTION OF THE DRAWINGS

Figure 1B:
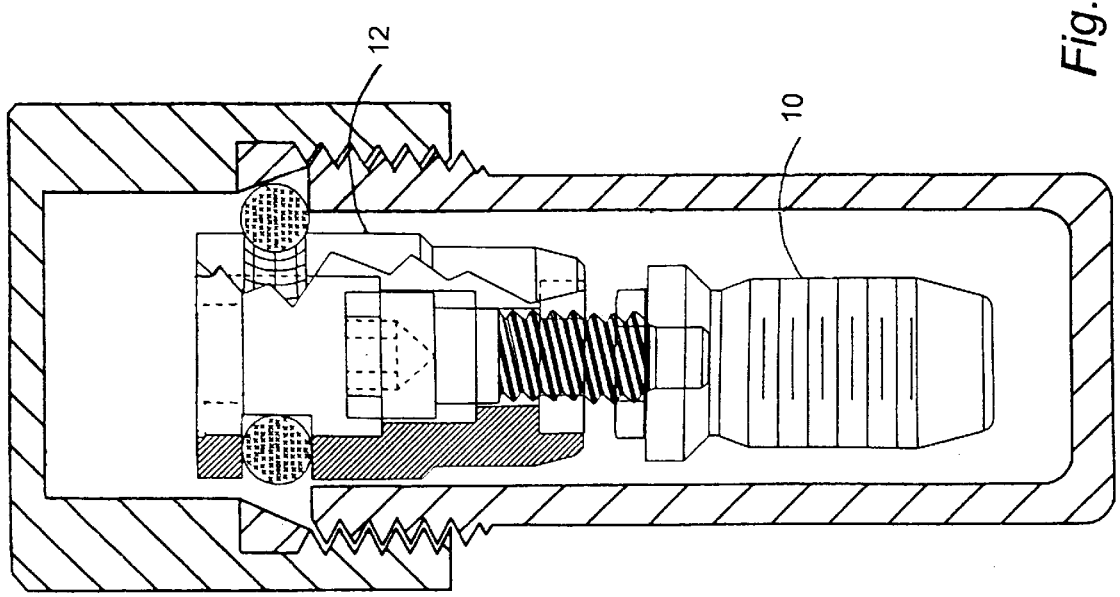
FIG. 1B illustrates the implant, carrier, and implant screw within a package.
Figure 1A:
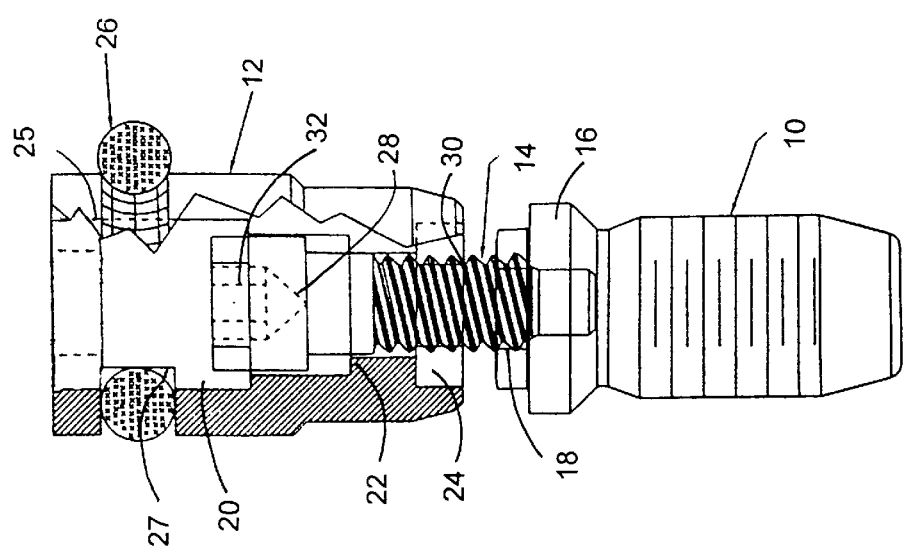
FIG. 1A illustrates an implant, a carrier, and an implant screw holding the carrier to the implant.

Referring initially to FIG. 1A, an implant 10 is attached to a carrier 12 with an implant screw 14. The implant 10 includes a non-circular manipulating fitting 16 which, as shown, is in the shape of a hexagon. Extending into the upper region of the implant 10 and through the manipulating fitting 16 is a threaded bore 18.

The carrier 12 has a through-bore 20 extending from its upper end to its lower end. The through-bore 20 has various sections. A shoulder 22 is positioned within the through-bore 20 near the lower end of carrier 12. Also located at the lower end of the through-bore 20 is an implant socket 24 that is configured to mate with the manipulating fitting 16 of the implant 10. At the upper end of the carrier 12 is another socket 25 which, as described below, engages the guide portion of the driver and also may receive a mounting section of an impression coping.. The socket 25 includes a non-circular internal surface (usually hexagonal) for non-rotational engagement with the driver and the coping.

An O-ring 26 is positioned within a groove 27 on the exterior surface of the carrier 12. Typically, the O-ring 26 is a polymer or an elastomer so that it is somewhat resilient. As shown in FIG. 1B, the O-ring 26 engages a ledge within a package containing the combination of the implant 10 and carrier 12 such that only the O-ring 26 contacts the package. Consequently, the carrier 12 and implant 10 are suspended in the package away from the walls so that the likelihood that either the implant 10 or the carrier 12 will become contaminated is greatly reduced. One type of suitable packaging arrangement is disclosed in U.S. Pat. No. 5,582,299 entitled "Dental Implant Packaging" which is herein incorporated by reference in its entirety.

Furthermore, the groove 27 does not have an entirely circular cross-section as can be seen in FIG. 1A by the fact that O-ring 27 is not centered on the central axis of the carrier 12. Instead, the groove 27 includes a region that is cut into the carrier 12 such that the cut section enters the socket 25. In other words, the groove 27 includes a hole which allows access into the socket 25. Consequently, the O-ring 26 includes a portion that rests within the socket 25 which, as will be described below, assists in retaining tools within the socket 25.

The implant screw 14 includes a head 28 that engages the shoulder 22 of the carrier 12. The implant screw 14 also includes a threaded shaft 30 which threadably engages the threaded bore 18 of the implant 10. Thus, after manufacturing the implant and carrier 12 and prior to packaging these two components, the manufacturer attaches these two components by use of the implant screw 14. In its final position (not shown), the implant screw 14 forces the lower end of the carrier 12 into contact with the upper surface of the implant 10 as the implant socket 24 envelops over the manipulating fitting 16 of the implant 10.

The implant screw 14 also includes within its head 28 a driver socket 32. The driver socket 32 is engaged by the driver tool which attaches the implant screw 14 to or removes the implant screw 14 from the assembly. When the implant screw 14 is removed, the carrier 12 can be released from the implant 10.

Because of the size of the implant screw 14, it is difficult to handle especially when doing so in a patient's mouth. Consequently, after the implant screw 14 is placed within the through-bore 20 to attach the implant 10 to the carrier 12, the O-ring 26 is inserted within the groove 27 such that a portion of the O-ring 26 enters the through-bore 20 in the area of the socket 25. The O-ring 26 protrudes inward toward the central axis of the carrier 12 far enough to reduce the effective diameter of the through-bore 20 to a dimension that is less than the dimension of the head of the implant screw 14. Thus, the implant screw 14 is held captive in the carrier 12 between the O-ring 26 and the shoulder 22. Alternatively, the through-bore 20 of the carrier 12 can be manufactured in a manner which causes an irregularity on its surface after the implant screw 14 is placed therein to effectuate the captivity of the implant screw 14.

Figure 2C:
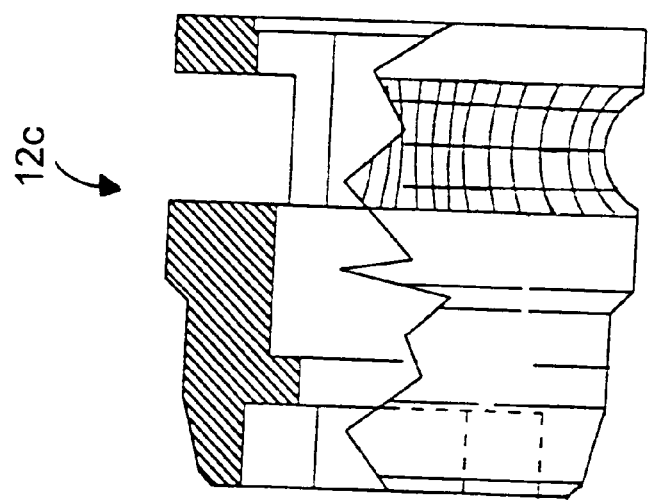
FIGS. 2A–2C illustrate a series of carriers having various lengths.
Figure 2A:
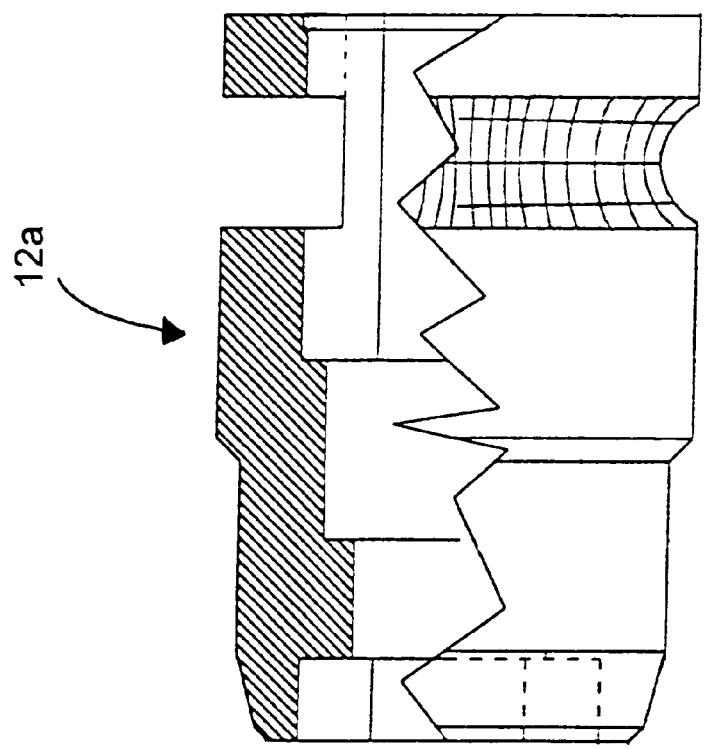
Figure 2B:
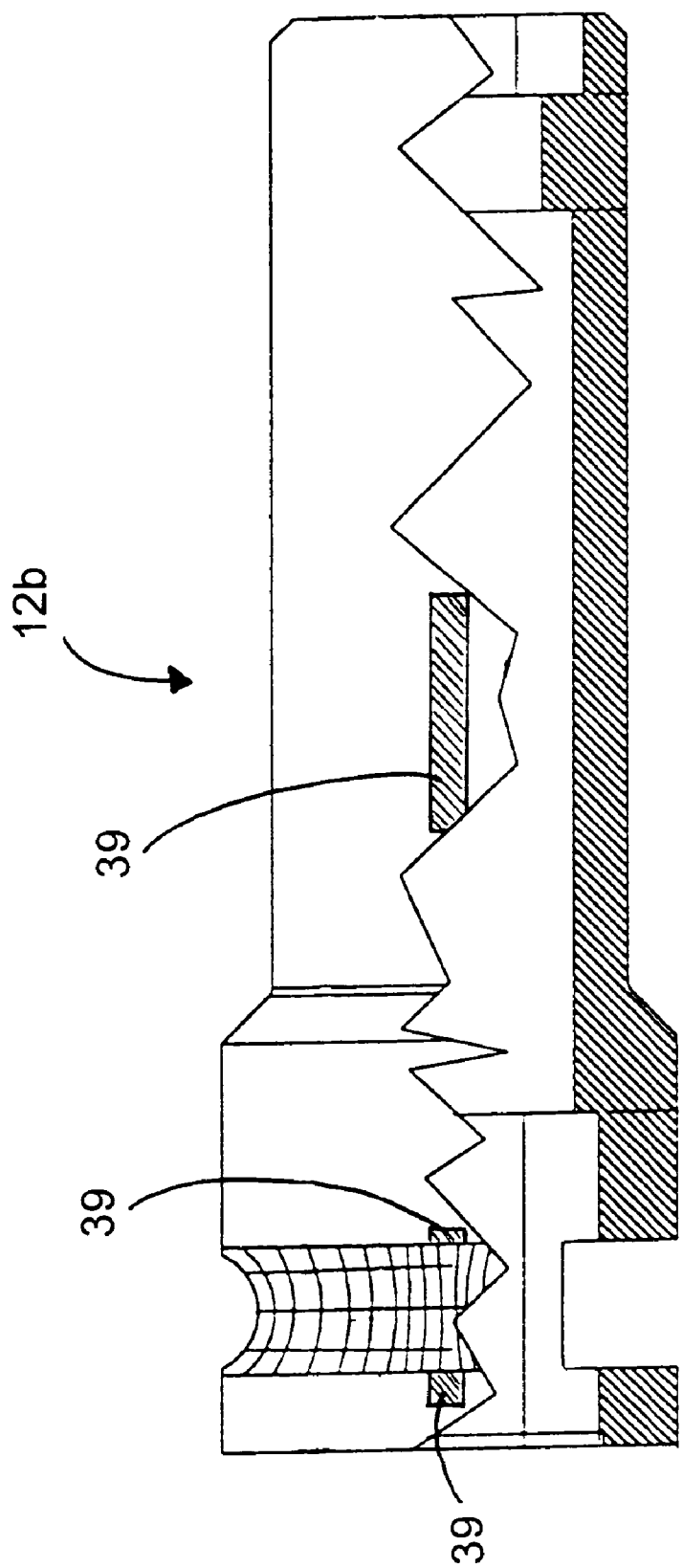

Depending on the conditions in the patient's mouth, the implant size is selected by the clinician that best suits the patient's condition. To assist the clinician with installing the implant properly, the carrier 12 is manufactured in various lengths as shown in FIGS. 2A–2C. In FIG. 2A, the carrier 12a, which includes all of the elements of carrier 12 shown in FIG. 1, is of an average length. In FIG. 2B, the carrier 12b is of a large length. Again, carrier 12b includes all of the elements of carrier 12 in FIG. 1 and also includes reference markings 39. These markings 39 are aligned with the faces of the implant socket 24. Thus, when inserting the carrier 12 and implant 10 into the bone, the clinician can visualize the orientation of the faces of the manipulating fitting 16 relative to the jawbone through the use of these markings 39.

In FIG. 2C, the carrier 12c is of a short length but contains all of the elements of carrier 12 in FIG. 1. Because of the variety of lengths in which the carrier 12 can be manufactured, the manufacturer chooses a carrier length that functions the best with the implant to which the carrier 12 is attached. As an example of the carrier sizes, the carrier 12a may be approximately 7.5 mm, carrier 12b about 15 mm, and carrier 12c about 5.0 mm. The width of each carrier 12a, 12b, and 12c is about 5 mm.

Figures 3A, 3B:
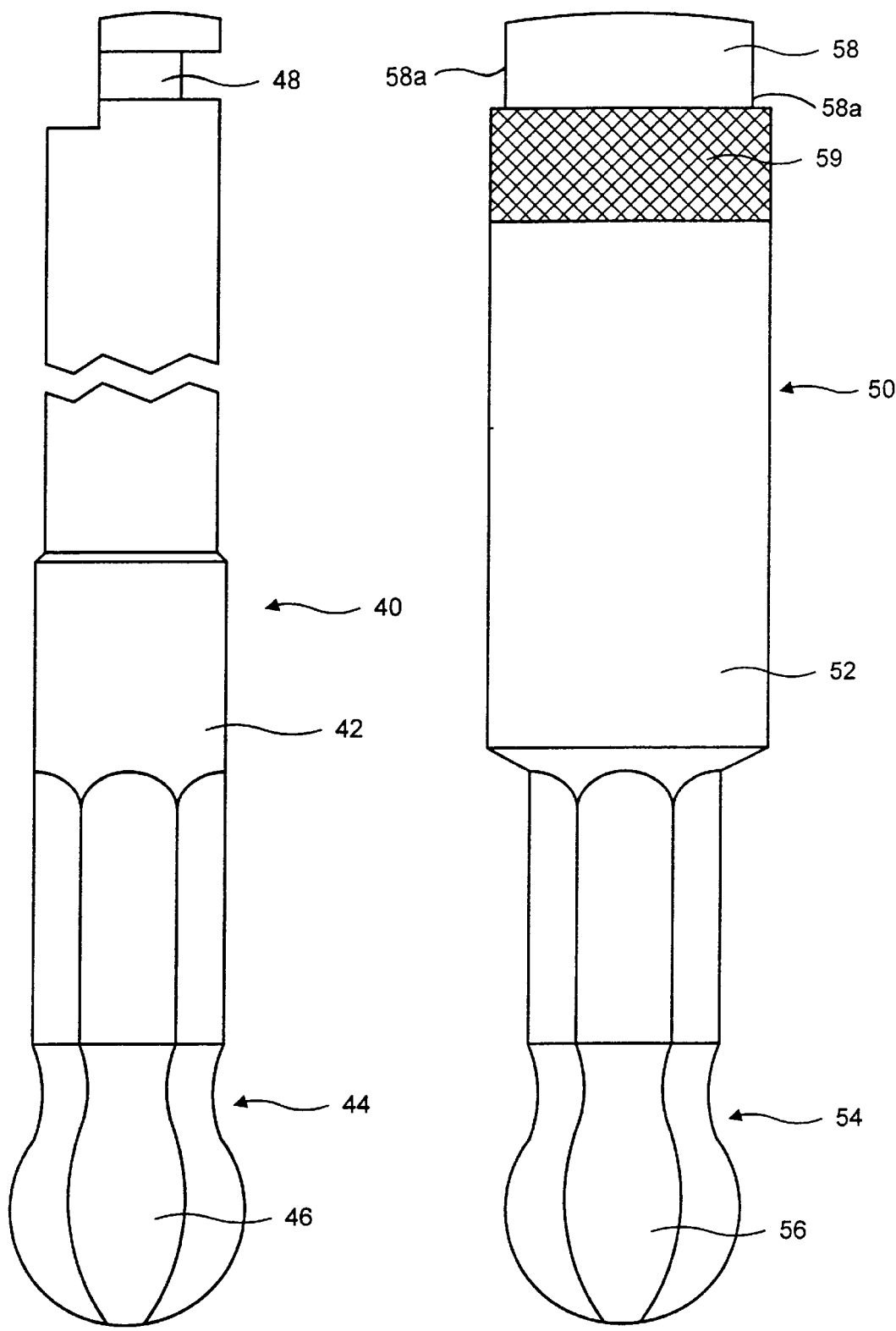
FIGS. 3A–3B illustrate two types of coupling tools that can impart rotational movement on the combination of the implant and the carrier.

FIGS. 3A and 3B illustrate tools that engage the combination of the implant 10 and carrier 12 to install the implant 10 within the jawbone. In FIG. 3A, a tool 40 includes a shaft 42 having at its lower end a ball-hex fitting 44. The ball-hex fitting 44 has six surfaces 46 positioned circumferentially around the fitting 44. The upper end of the shaft 42 includes a connecting arrangement 48 that allows the tool 40 to be coupled to a power driver such as a common dental hand piece. Thus, as the power driver operates, the tool 40 rotates and imparts rotational movement on the carrier 12 and implant 10. A cross-section of the ball-hex fitting 44 at its maximum diameter has approximately the same cross-section of the socket 25 in carrier 12.

In FIG. 3B, an alternative tool 50 is illustrated. Tool 50 includes a shaft 52 having at its lower end a ball-hex fitting 54. The ball-hex fitting 54 includes six surfaces 56 positioned circumferentially therearound. The upper end of the tool 50 has flat engagement surfaces 58 which meet at corners 58a. The flat engagement surfaces 58 (shown here as four flat surfaces) engage a manual rotating mechanism such as a dental wrench. Also located at the upper portion of the tool 50 is a knurled surface 59 which the clinician grasps when rotating the combination of the implant 10 and carrier 12 initially into the site of the jawbone. Again, a cross-section of the ball-hex fitting 54 at its maximum diameter should have approximately the same cross-section of the socket 25 in carrier 12. Thus, tool 50 differs from tool 40 in that tool 50 is designed for installing the implant 10 into its final position within the jawbone through non-power driven means.

In operation, the clinician selects the tool 40 or 50 that is best suited for the conditions in the patient's mouth. For example, if the clinician knows that the implant 10 will be installed through dense bone, then additional torque is needed. Thus, the clinician will likely choose tool 40 which can be engaged by a power driver. Alternatively, if the clinician understands the bone tissue in which the implant 10 will be installed in cancellous bone, the clinician may instead choose tool 50 and not utilize a power driver.

In any event, after choosing the tool 40 or 50 that is best suited for the patient's conditions, the clinician grasps the upper end of the tool 40 or 50 and inserts the ball-hex fitting 44 or 54 into the socket 25 of the carrier 12. Consequently, tools 40 and 50 are devices that can be used by the clinician to transport the combination of the implant 10 and the carrier 12 from its package to the site in the patient's mouth. The portion of the O-ring 26 which extends into the socket 25 assists in retaining the ball-hex fitting 44 or 54 within the socket 25. Preferably, the O-ring 26 reduces the effective diameter of the socket 25 to a dimension which is less than the maximum dimension of the ball-hex fitting 44 or 54. Once the ball-hex fitting 44 is inserted into the socket 25 and past the flexible O-ring 26, the combination of the carrier 12 and the implant 10 can be transported by the tool 40 or 50.

Alternatively, the clinician may feel more comfortable using the wider tool 50 having the knurled surface 59 and choose to use tool 50 to transport the combination of the implant 10 and carrier 12 from its package to the installation site. Then, the clinician may replace tool 50 with tool 40 and utilize the power driver which rotates tool 40. In this alternative methodology, utilization of tool 50 may allow the clinician the ability to start the implant 10 into the jawbone by rotating tool 50 with his or her fingers.

The tools 40 and 50 can be made in various lengths. Therefore, the clinician no longer needs to substitute the packaged carrier for a longer or shorter carrier to suit the conditions in the patient's mouth as has been the case in many prior art systems. Instead, the clinician simply chooses the length of tool 40 or 50 that will best assist him or her in the installation process.

Figure 4:
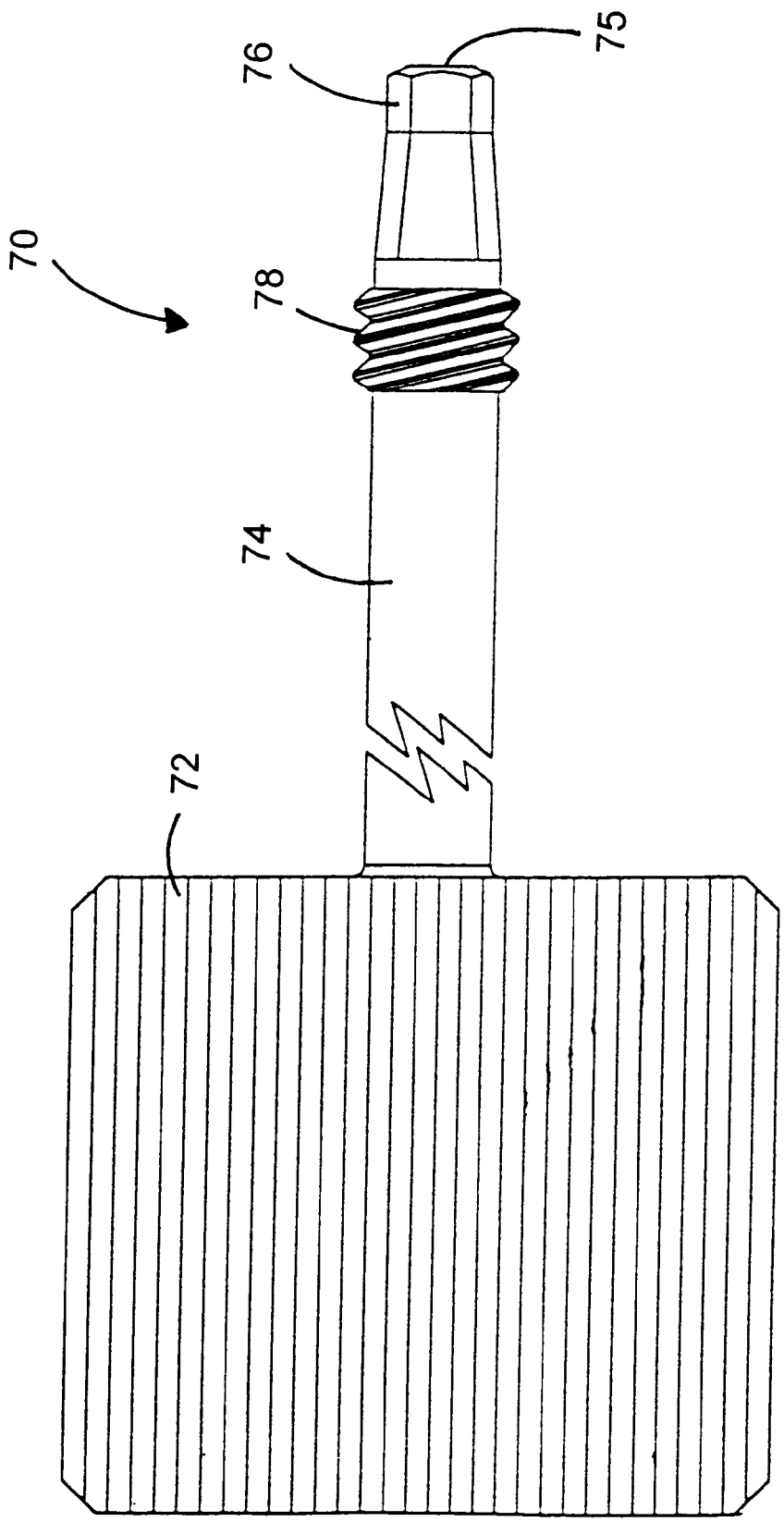
FIG. 4 illustrates a driver that is used to engage and disengage the implant screw.

Referring now to FIG. 4, a driver 70 for use in removing the carrier 12 from and attaching the carrier 12 to the implant 10 is illustrated. The driver 70 includes a head portion 72 which the clinician grasps with his or her fingers. Below the head portion 72 is a shank 74 that extends downwardly to a lower end 75. Adjacent the lower end is a fitting 76 having a plurality of sides which fits within the driver socket 32 of the implant screw 14 (FIG. 1). The fitting 76 expands outwardly along the shank 74 from the lower end 75 toward the head 72. This allows for easy insertion of the lower end 75 and fitting 76 into the corresponding driver socket 32 of the implant screw 14. Furthermore, the angled section of the fitting 76 allows for a tight, press-fit engagement of the driver 70 in the driver socket 32 of the implant screw 14. The details of such this angled configuration of the driver 70 are disclosed in U.S. Pat. No. 5,105,690 entitled "Manipulator-Driver for Holding and Driving a Screw-Type Article" which is herein incorporated by reference. Additionally, the shank 74 includes a threaded portion 78 which retains a guide thereon as described below with reference to FIGS. 5 and 6.

Figures 5A, 5B:
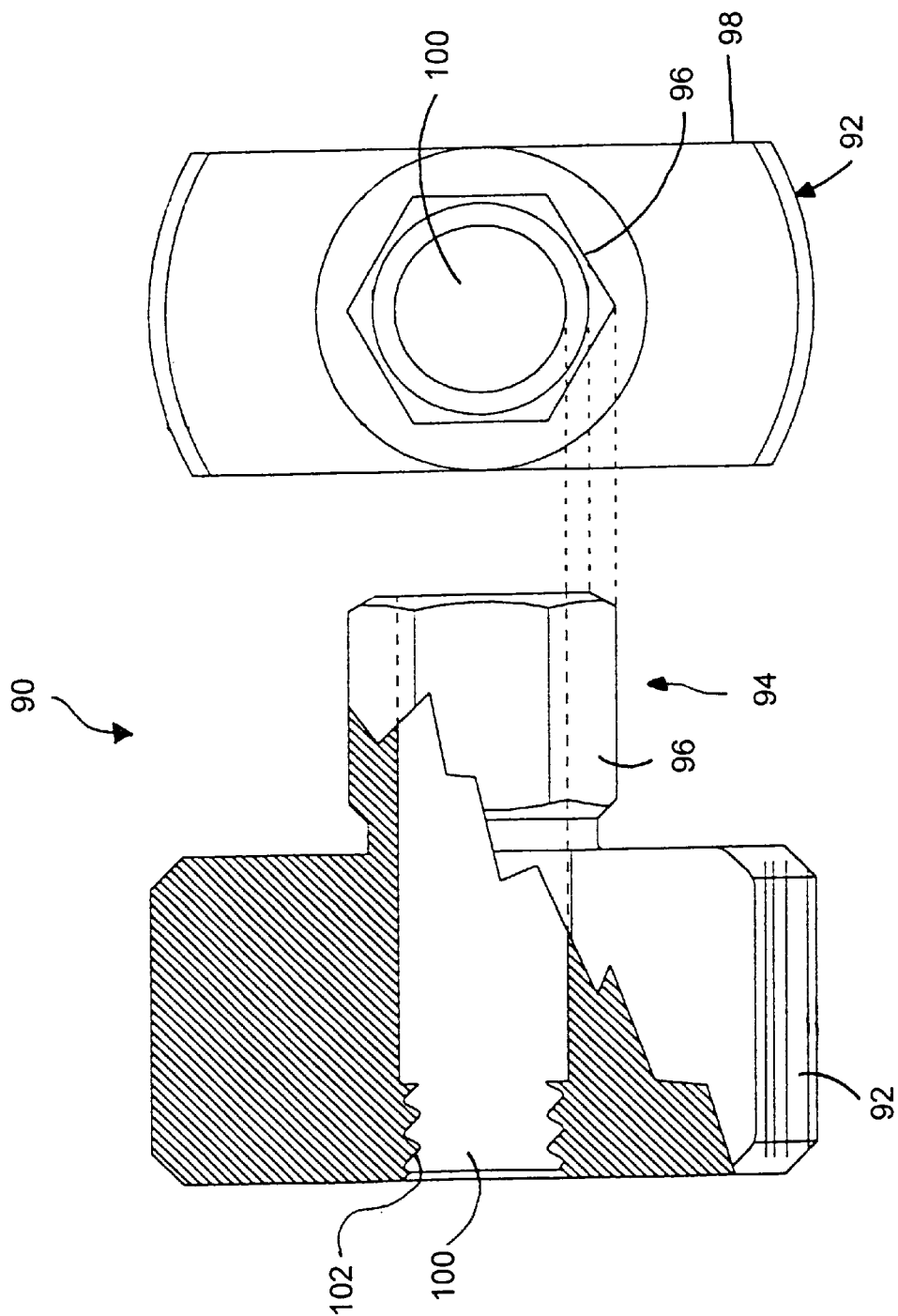
FIGS. 5A–5B illustrate a guide that is used in conjunction with the driver in FIG. 4 to hold the carrier against rotation while manipulating the implant screw.

FIGS. 5A and 5B are partially broken-away side and bottom views, respectively, of a guide 90 that is used in conjunction with the driver 70 of FIG. 4. The guide 90 includes a main body 92 at one end and an engaging portion 94 at the other end. The main body 92 may have a surface which is knurled to allow the clinician a region for grasping. The engaging portion 94 includes a plurality of side surfaces 96 which give the engaging portion 94 a non-circular cross-sectional shape (e.g. hexagonal as shown). As can be best seen in FIG. 5B, main body 92 includes two opposing flats 98 which, as described below, provide surfaces which a tool such as a wrench may engage.

Extending through the main body 92 and the engaging portion 94 of the guide 90 is a hole 100. The hole 100 includes a threaded region 102 which matches the thread type of threaded portion 78 on driver 70. As is shown in FIG. 7, the threaded region 102 permits the guide 90 to be retained on the shank 74 of driver 70 thereby reducing the risk that the guide 90 will become detached therefrom.

Figure 6:
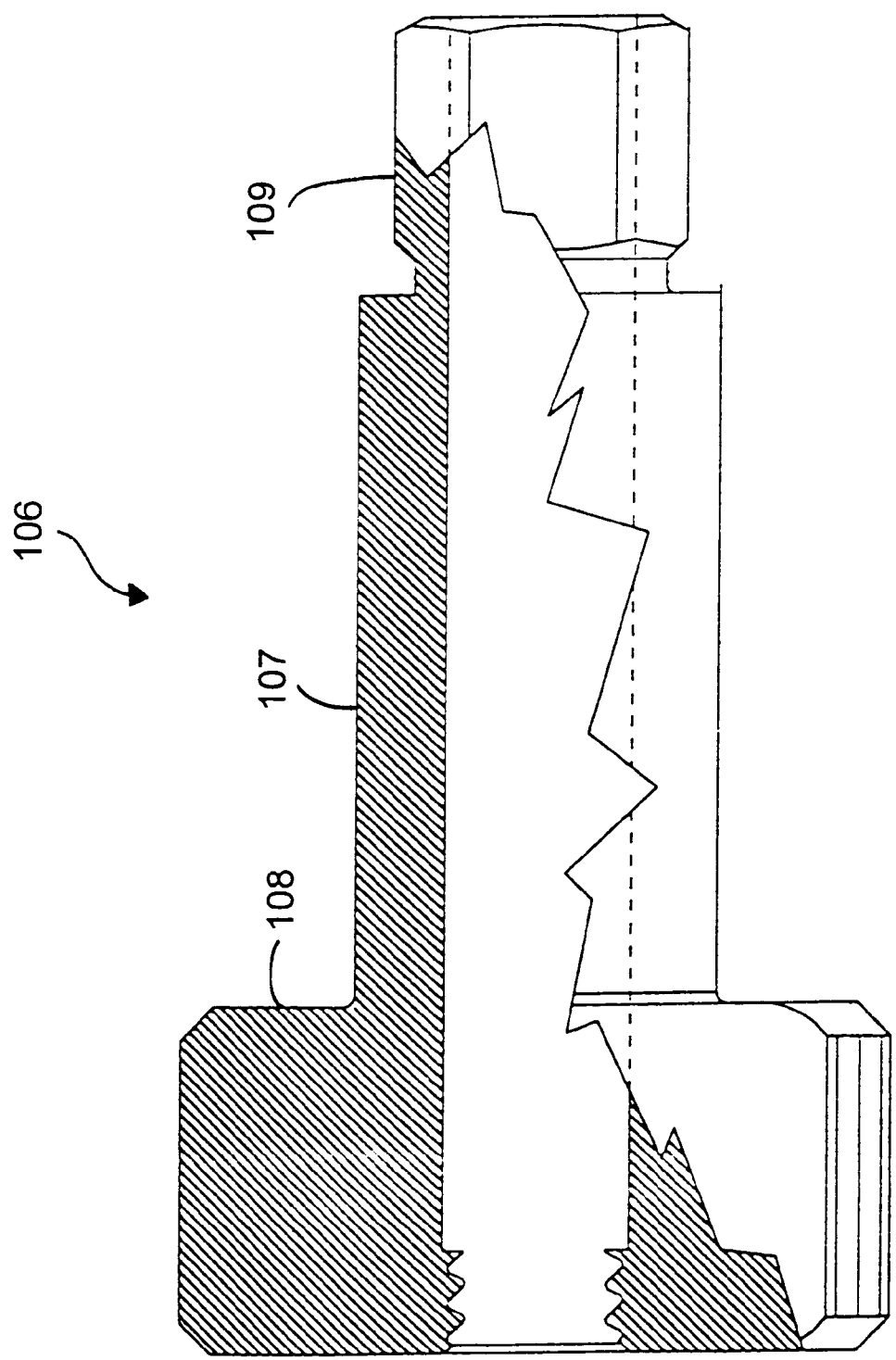
FIG. 6 illustrates an alternative guide similar to the one illustrated in FIGS. 5A–5B.

FIG. 6 is a partially broken-away, side view of an alternative guide 106 that is similar to guide 90 in FIGS. 5A and 5B. However, the guide 106 of FIG. 6 also includes an extended shaft 107 separating the main body 108 from the engaging portion 109. Thus, the guides may be manufactured in a variety of lengths. Thus, the clinician can choose the guide that best suits the needs of the patient.

Figure 7:
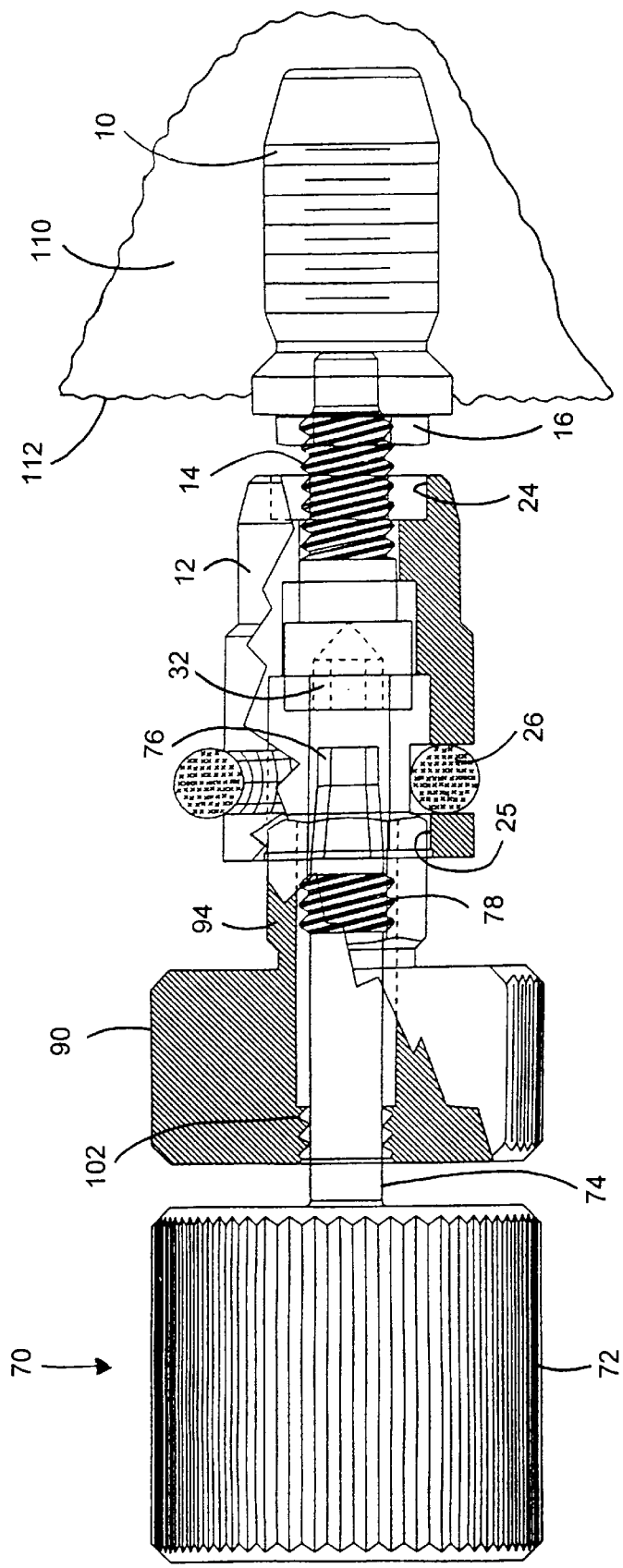
FIG. 7 illustrates the driver FIG. 4 and the guide of FIGS. 5A–5B releasing the implant screw from the implant.

FIG. 7 illustrates, in an exploded view, the process of the carrier 12 being removed from the implant 10 after the implant 10 is installed into its final position in bone 110 with the upper flange portion of the implant 10 being near the upper surface 112 of the bone 110. To remove the carrier 12 from the implant 10, the driver 70 with the selected guide 90 is placed above and in axial alignment with the combination of the carrier 12 and implant 10. The combination of the driver 70 and the guide 90 is then lowered such that engaging portion 94 of the guide 90 fits within socket 25 of the carrier 12. Due to the non-rotational engagement of the engaging portion 94 and the socket 24, the guide 90 does not rotate relative to the carrier 12. Although the engaging portion 94 of the guide 90 is partially set out from the socket 25 in the exploded view of FIG. 7, the engaging portion 94 is usually inserted entirely in the socket 25. Consequently, a section of the engaging portion 94 contacts the O-ring 26. Furthermore, the engaging portion 94 may have an circumferential groove into which the O-ring 26 would be positioned (like groove 131 in FIG. 8A).

The clinician then pushes the head 72 of driver 70 downwardly such that fitting 76 on the lower portion of shank 74 is forced into non-rotational engagement with the driver socket 32 of implant screw 14. Because of its unique tapered shape, the fitting 76 fits within the driver socket 32 without the need for an excessive amount of force or rotation. With the clinician grasping the head 72 and the flats 98 (FIG. 5B) of guide 90, the clinician then rotates head 72 while holding guide 90 non-rotationally. Because guide 90 is non-rotationally attached to the carrier 12 which is itself non-rotationally attached to the implant 10 through implant socket 24 and manipulating fitting 16, any rotation imparted on head 72 causes only the implant screw 14 to rotate; the implant 10 does not rotate. In other words, guide 90 holds the assembly of the carrier 12 and implant 10 steady as the implant screw 14 is removed or installed.

As the implant screw 14 rotates, it is threaded out of the implant 10 such that there is no component holding carrier 12 onto implant 10. Additionally, because there is no rotation imparted on the implant 10, its final installation position within bone 110 remains constant. When the implant screw 14 is fully unthreaded from implant 10, the driver 70 and guide 90 are removed from the patient's mouth. Because the carrier 12 is now free of the implant 10, the axial movement of the driver 70 and guide 90 also removes the carrier 12 because of the tight fit of the engaging portion 94 in the socket 25 due to the contact with the O-ring 26. If the O-ring 26 is not designed to provide tight engagement with the engaging portion 94, then the clinician simply releases the carrier 12 from implant 10 and removes it from the mouth once the implant screw 14 has been threadably removed from the implant 10.

In the event that the clinician finds it difficult to grasp the guide 90 and restrain it from rotational movement, the clinician can utilize another tool, such as a wrench, to grasp the two flats 98 (FIG. 5B) such that the clinician's fingers are only needed to manipulate the head 72 of driver 70. In this situation, one of the clinician's hands is holding the wrench while the other is simply unscrewing the implant screw 14 with the driver 70.

The relationship of the threaded region 102 of the guide 90 and the threaded portion 78 of the driver 70 is shown in FIG. 7. Once the threaded region 102 of the guide 90 is threaded over the threaded portion 78 on the shank 74 of driver 70, the guide 90 cannot be removed from the driver 70 without rotating the guide 90 relative to driver 70 while the threaded region 102 is positioned directly adjacent to the threaded portion 78. In essence, the guide 90 is held captive on the driver 70 between the threaded portion 78 and the head 72. In typical operation as the clinician is utilizing the driver 70 and guide 90 to remove the implant screw 14 from the implant, the threaded region 102 is axially spaced from the threaded portion 78. Thus, the rotation of the driver 70 relative to the guide 90 in that situation does not cause engagement of the threaded region 102 and the threaded portion 78. The guide 90 is not released from the driver 70 during removal or insertion of the implant screw 14 due to the positioning of threaded portion 78 and threaded region 102.

Until now, the discussion has focused on the installation of the implant 10 and removal of the carrier 12 therefrom after installation. However, the combination of the implant 10 and carrier 12 can also be used with additional components to take an impression of the patient's mouth during first-stage surgery after the implant 10 has been installed into its final position within the jawbone. The components used to perform this function are described with reference to FIGS. 8–11.

Figure 8B:
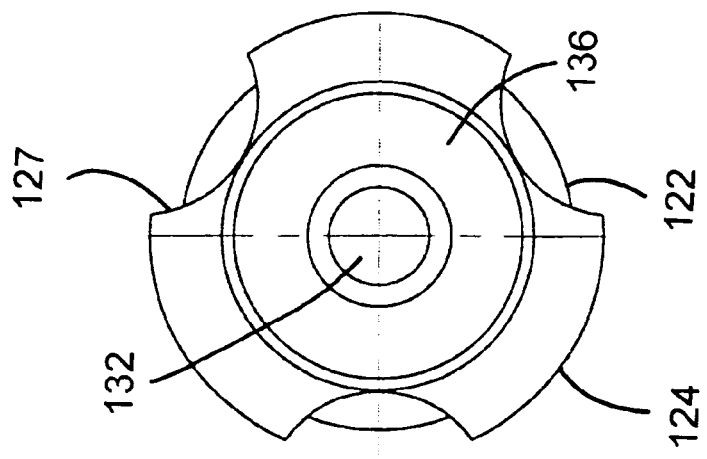
FIGS. 8A–8B illustrate an impression coping that can be attached to the carrier of the present invention.
Figure 8A:
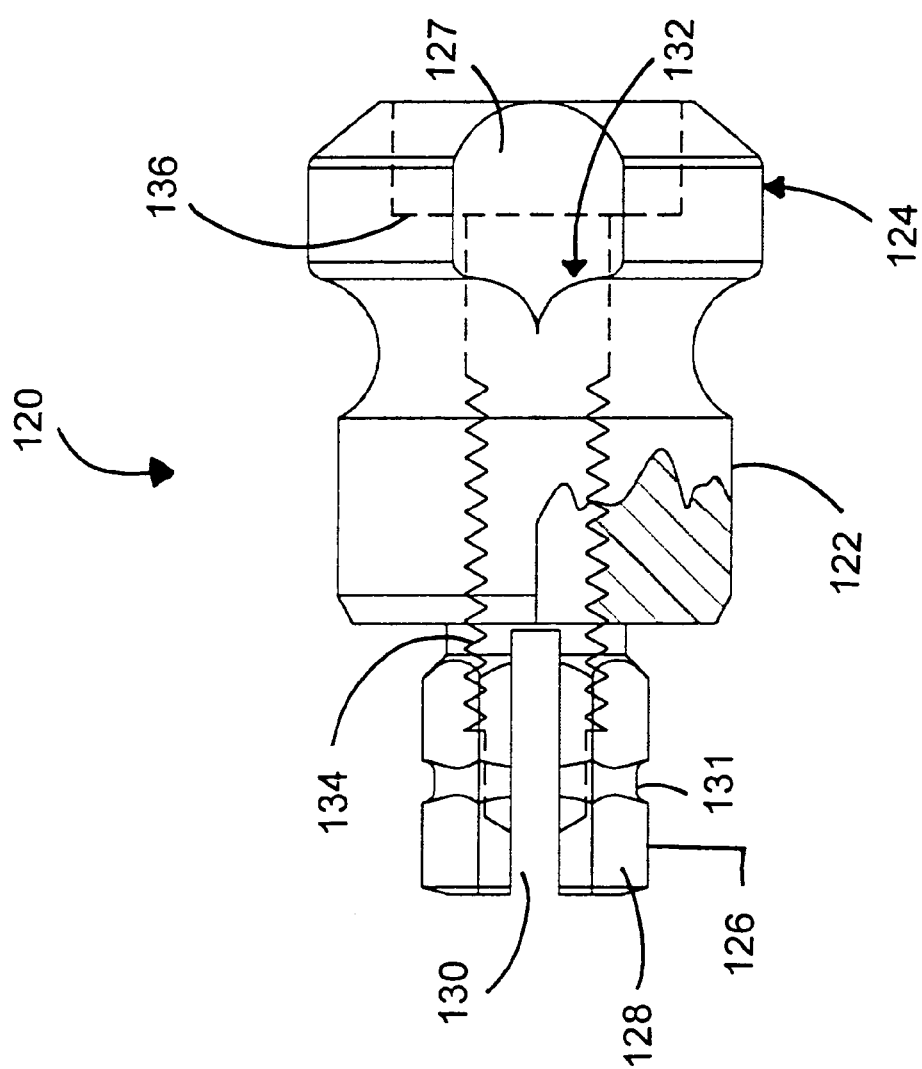

In FIG. 8, an impression coping 120 is illustrated. The impression coping 120 includes a body 122 which separates an indexing region 124 from a boss 126 that engages the carrier 12. The indexing region 124 includes a plurality of recesses 127 which are shown best in FIG. 8B. The recesses 127 form in the overlying impression material a unique shape which allows for the proper orientation of the impression coping 120 when it is reinserted into the impression material after the impression is taken. The recesses 127 are circumferentially symmetric about the central axis of the impression coping 120 and each recess 127 is aligned with a corresponding face 128 on the boss 126. The details of this impression coping 120 and its associated bolts are found in U.S. Pat. No. 5,685,715 entitled "Self-Indexing Transfer Impression Coping" which is herein incorporated by reference.

The plurality of faces 128 give the boss 126 a non-round cross-sectional shape. Because the boss 126 is to be inserted into the socket 25 (FIG. 1) of the carrier 12, the boss 126 has the same cross-sectional configuration as the socket 25. Additionally, boss 126 includes a slit 130 extending therethrough. The slit 130 allows for the expandability of the boss 126 when it is engaged by the bolt described below in FIGS. 9 and 10. To further assist in retention of the coping 120 on the carrier 12, a groove 131 may extend circumferentially around the boss 126 and engages the O-ring 26 within the socket 25 to assist in locking the impression coping 120 on the carrier 12. In any event, the lower end surface of the body 122 is to engage the upper end surface of the carrier 12 adjacent to the opening of the socket 25.

A bore 132 extends through the body 122, the indexing region 124, and the boss 126. The bore 132 includes a threaded portion 134 for threadably engaging a corresponding threaded region of the bolt which mates with the impression coping 120. Within the indexing region 124 is an annular ledge 136 for engaging the head of the bolt. The annular ledge 136 is best seen in FIG. 8B and is manufactured in various sizes depending on the size of the bolt to be used with the coping 120. As described below with reference to FIGS. 9 and 10, the impression coping 120 can be used as both a "transfer coping" and a "pick-up coping."

In FIG. 9, a pick-up bolt 140 is illustrated. The pick-up bolt 140 includes an elongated head 142 connected to a shaft 144 having at its lower end a threaded region 145. At the upper end of the elongated head 142 is a knurled portion 146 which is a surface the clinician can easily grip. The elongated head 142 also includes an internal fitting 148 to mate with a correspondingly shaped tool, such as the fitting 76 of driver 70.

When the pick-up bolt 140 is used with impression coping 120, the boss 126 of the impression coping 120 is first inserted into the upper end of carrier 12 at its socket 25. The pick-up bolt 140 is then inserted through the bore 132 of the impression coping 120. The threaded region 145 of the pick-up bolt 140 threadably engages the threaded portion 134 of the bore 132. As the pick-up bolt 140 is threaded into the impression coping 120, the threaded region 145 eventually reaches the threaded portion 134 located within the boss 126. As this occurs, the boss 126 is expanded radially outward such that it is forced into a press-fit, frictional engagement with the socket 25 of the carrier 12. Thus, the impression coping 120 is fixedly mounted on the carrier 12 by the use of this pick-up bolt 140. This allows the clinician to use an open tray method of making an impression whereby after the impression is taken, the pick-up bolt 140 is removed while the impression material remains at the site. The impression coping 120 is then "picked up" as the impression material is removed.

The carrier 12 is removed from the implant 10 and then reunited with the impression coping 120 within the impression material such that both the impression coping 120 and the carrier 12 are used to create the model used to develop the prosthetic tooth. The carrier 12 is attached to the implant analog that is used to produce the stone model replicating the patient's mouth.

In FIG. 10, a transfer bolt 150 is illustrated. The transfer bolt 150 includes a short head 152, a shank 154, and a threaded region 155 at the lower end of the shank 154 opposite the head 152. The short head 152 decreases in its diametric dimension from the region near the shank 154 to its outer extremity. The short head 152 may also include a groove 156 extending therearound allowing for additional retention of the transfer bolt 150 in the impression material. The diametric width of the short head 152 adjacent the shaft 154 is approximately the same as the diametric width of the annular ledge 136 of the impression coping 120. Thus, when transfer bolt 150 is used to affix impression coping 120 to carrier 12, the lower surface of the short head 152 engages the annular ledge 136.

When the transfer bolt 150 is used, the combination of the transfer bolt 150 and the impression coping 120 forms a "transfer-type" impression coping. After the threaded region 155 of the transfer bolt 150 is threadably engaged with the threaded portion 134 of the internal bore 132 of the impression coping 120, an impression is taken using a closed tray method. When the impression material is removed from the patient's mouth, the impression coping 120 and the transfer bolt 150 both remain on the carrier 12. The clinician then removes the transfer bolt 150 by rotating head 152 such that the threaded region 155 is threadably released from the threaded portion 134 of the impression coping 120. Once the transfer bolt 150 is removed from the patient's mouth, the impression coping 120 can be removed. The clinician then releases the carrier 12 from the implant 10 as described previously, and reunites impression coping 120 on the carrier 12 by the use of the transfer bolt 150. The combination of the transfer bolt 150, impression coping 120 and carrier 12 is then attached to an implant analog in the laboratory. The impression material is then reinserted over the transfer bolt 150, impression coping 120 and carrier 12 such that a stone model can be build which replicates the prevailing conditions in the patient's mouth.

It should be noted that transfer bolt 150 can be screwed onto and removed from the impression coping by use of a tool which has a tapering socket that replicates the tapering of the short head 152. Such a tool may also include a retention O-ring which engages the groove 156 thereby locking the tool onto the transfer bolt 150. Thus, the clinician can easily attach and remove the transfer bolt 150 from the impression coping 120. A corresponding taper could be used on the pick-up bolt 140 at its upper end so that the same tool could be used with both the pick-up bolt 140 and transfer bolt 150.

As can be seen, the impression coping 120 is a very versatile component in that it can be used as both a transfer-type coping and a pick-up type impression coping, depending on the bolt used. Additionally, because the recesses 127 of impression coping 120 are aligned with faces 128, the recesses 127 are also aligned with the manipulating fitting 16 of the implant 10 (FIG. 1). This is due to the fact that the socket 25 of the carrier 12 has its surfaces aligned with the implant socket surfaces 24. Because each recess 127 is aligned with a corresponding face 128 and socket 25 is aligned with manipulating fitting 16, the combination of the impression coping 120 and the carrier 12 can easily be oriented in the impression material correctly when the carrier 12 and impression coping 120 are mounted on the implant analog. Actually, after the carrier 12 and coping 120 are attached, three of the possible six orientations on the implant analog will yield the correct orientation due to the symmetry.

Figures 11A, 11B:
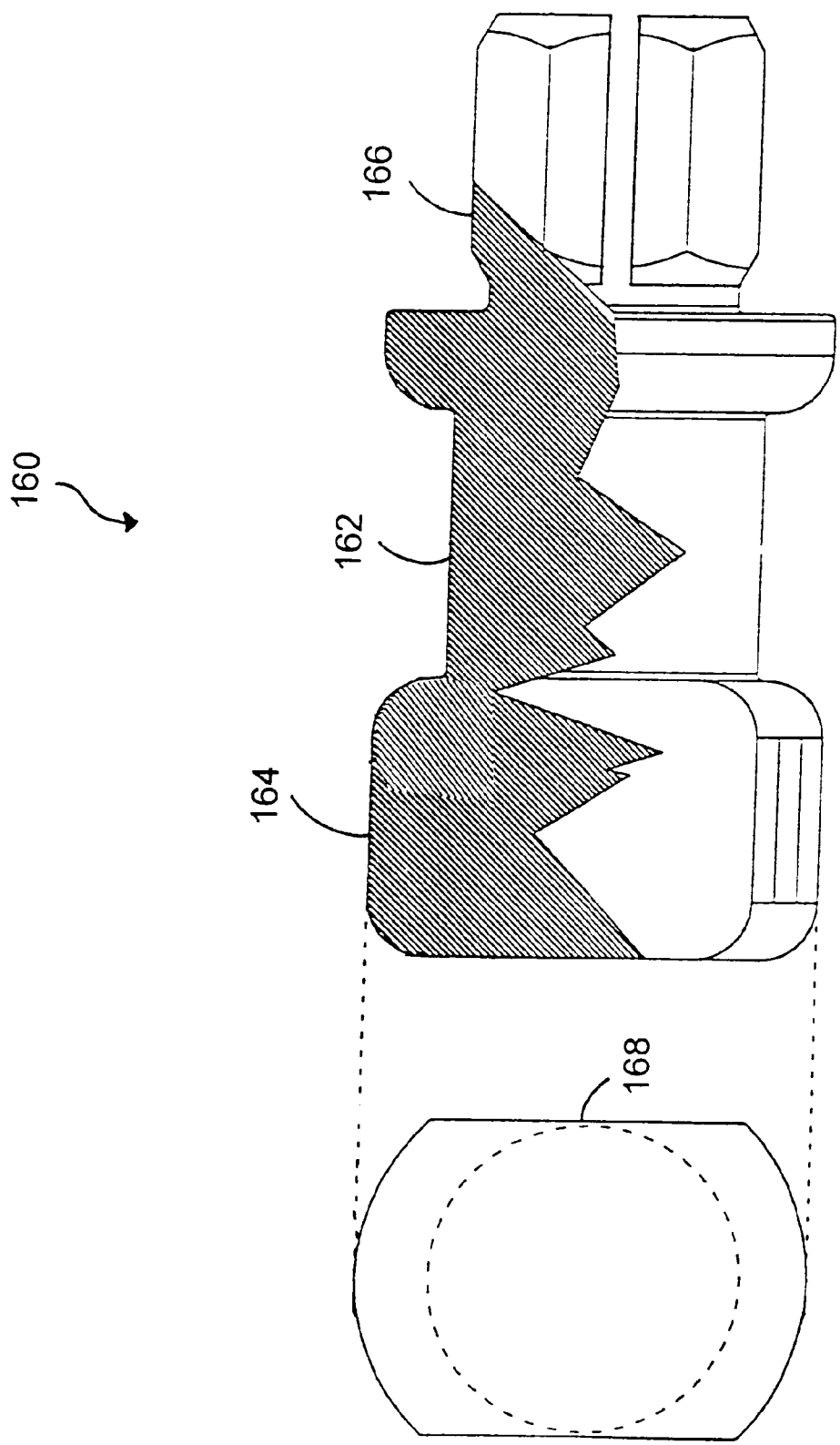
FIGS. 11A and 11B illustrate an alternative pick-up impression coping that can be used with the carrier of the present invention.

In FIGS. 11A and 11B, an alternative pick-up coping 160 is illustrated. The pickup coping 160 includes a body 162 which separates a head portion 164 from an expandable boss 166. The head portion 164 includes a pair of flats 168 allowing for the indexing of the pick-up coping 160 within the impression material. As with the previously described impression coping 120, the boss 166 expands outwardly when the pick-up bolt 140 in FIG. 9 is threaded therein. Thus, although not illustrated, the pick-up coping includes an internally threaded bore whose threads extend into the region of the boss 166. The pick-up coping 160 can utilize the same impression techniques as those described with reference to FIG. 9. Although the expandable boss 166 does not show a circumferential groove as did the impression coping 120, the expandable boss 166 in the pick-up coping 160 may include a similar groove to assist in locking the expandable boss 166 within the socket 25 of the carrier 12 through engagement with the O-ring 26.

As has been stated previously, once the implant 10 has been installed into its final position within the living jawbone, there are two methods which can be employed by the clinician utilizing the components described in FIGS. 1–11. First, the clinician can simply remove the carrier 12 from the implant 10. Alternatively, the clinician can attach the impression coping 120 to the carrier 12 and take an impression of the areas around the impression coping 120 and carrier 12 immediately above the implant 10. If the latter option is employed by the clinician, the clinician then removes the impression coping 120 and the carrier 12 and reunites these two components before reinserting them back into the impression material.

Regardless of the method chosen by the clinician, the result is an implant 10 fully inserted into the jawbone with the overlying gingiva having therethrough an aperture that exposes the manipulating fitting 16 of the implant 10. To complete the first-stage surgery, the clinician installs onto the implant 10 a commonly known healing cap which covers the threaded bore 18 (FIG. 1). The overlying gingiva is then sutured to allow for its healing as well as the osseointegration of the implant 10.

During typical stage-two surgery, the gingiva overlying the implant 10 is reopened so as to expose the healing cap positioned on the implant 10. The healing cap is then removed and a gingival healing abutment is attached to the implant 10. This allows for the healing of the gingiva tissue around the healing abutment directly above the implant 10 to a shape that is preferably similar to the profile from which the natural tooth emerged from the gingiva.

If an impression was taken during first-stage surgery, the clinician will have had time to develop a prosthetic tooth. Instead of utilizing a healing abutment, the clinician can install the prosthetic tooth directly on the implant. Usually, this prosthetic tooth is a temporary one and another impression may be taken to develop an accurate final dentition.

But, in some situations where the final position of the overlying gingiva can be predicted, the artificial tooth that is replicated from the model produced in first-stage surgery can be so accurate that a permanent dentition can be developed and installed onto the implant 10 at second-stage surgery. In this situation, the patient enters the clinician's office only twice; the first time for installing the implant, the second time for installing the permanent dentition.

We claim:

1. A set of components for delivering an implant to a site in living jawbone at which said implant is to be installed, said implant having a gingival end with a manipulating fitting and a threaded bore extending inwardly from said gingival end, said set comprising:
   a carrier device having an upper end, a lower end, a through-bore extending between said lower and upper ends, and a fitting for mating with said manipulating fitting of said implant, said through-bore in the region adjacent to said upper end including a non-circular socket for receiving an implant-insertion tool imparting movement to said carrier device and said implant; and
   an implant screw for attaching said carrier device to said implant, said implant screw having a lower threaded portion for engaging said threaded bore of said implant and a head for stopping on a shoulder within said through-bore of said carrier device;
   and wherein said carrier device further includes means for captivating said head of said implant screw within said through-bore of said carrier.

2. The set of components of claim 1, wherein said carrier device further includes means for holding said carrier and said implant in suspension within a sterilized package.

3. The set of components of claim 2, wherein said holding means is an O-ring positioned around said carrier device.

4. The set of components of claim 1, wherein said captivating means includes a structure protruding into said through-bore and said shoulder.

5. The set of components of claim 4, wherein said structure is a portion of an O-ring.

6. The set of components of claim 1, wherein said carrier device further includes means for retaining said implant-insertion tool in said non-circular socket.

7. The set of components of claim 6, wherein said retaining means is positioned within said through-bore.

8. The set of components of claim 6, wherein said retaining means includes a rubber structure adjacent to said non-circular socket in said through-bore.

9. The set of components of claim 6, wherein said retaining means and said captivating means include the same structure.

10. The set of components of claim 1, wherein said carrier device includes means for referencing the orientation of said manipulating fitting of said implant.

11. The set of components of claim 1, wherein said shoulder of said carrier device is in a plane that is perpendicular to a central axis of said carrier device.

12. The set of components of claim 1, wherein said manipulating fitting is a hexagonal boss and said fitting on said carrier device is a hexagonal recess.

13. A set of dental components, comprising:
   an implant for installation in a site within living jawbone, said implant having a gingival end with a manipulating fitting and a threaded bore extending inwardly from said gingival end;
   a carrier device for delivering said implant to said site and assisting in inserting said implant in said jawbone, said carrier device having an upper end, a lower end engaging said gingival end of said implant, a through-bore extending between said lower and upper ends, and a fitting mating with said manipulating fitting of said implant, said through-bore in the region adjacent to said upper end including a non-circular socket for receiving an implant-insertion tool imparting movement to said carrier device and said implant, said carrier device further including means for visualizing an angular orientation of said manipulating fitting of said implant; and
   an implant screw attaching said carrier device to said implant, said implant screw having a lower threaded portion engaging said threaded bore of said implant and a head for stopping on a shoulder within said through-bore of said carrier device.

14. The set of components of claim 13, wherein said carrier device, said implant, and said implant screw are disposed in a sterile package for delivery, said carrier device including means for suspending said carrier device and said implant in said sterile package.

15. The set of components of claim 13, wherein said referencing means includes a marking on an exterior surface of said carrier between said upper and lower ends.

16. A set of components for delivering an implant to a site in living jawbone at which said implant is to be installed, said implant having a gingival end with a manipulating fitting and a threaded bore extending inwardly from said gingival end, said set comprising:
   a carrier device having an upper end, a lower end, a through-bore extending between said lower and upper ends, and a fitting for mating with said manipulating fitting of said implant, said through-bore in the region adjacent to said upper end including a non-circular socket;
   an implant screw for attaching said carrier device to said implant, said implant screw having a lower threaded portion for engaging said threaded bore of said implant and a head for stopping on a shoulder within said through-bore of said carrier device; and
   a tool for releasing said implant screw from said implant so as to detach said carrier device from said implant, said tool including means for prohibiting the rotation of said carrier device and means for imparting rotation to said implant screw, said rotational prohibiting means non-rotationally holding said carrier device while said implant screw is threadably released from said threaded bore of said implant, and wherein said carrier device include means for coupling said carrier device to said tool such that said carrier device remains coupled to said tool when said carrier device is detached from said implant.

17. The set of components of claim 16, wherein said rotational prohibiting means of said tool includes a non-circular protrusion mating with said non-circular socket in said carrier device.

18. The set of components of claim 16, wherein said tool includes two tool components, a first tool component includes said rotational prohibiting means and a second tool component includes rotational imparting means.

19. The set of components of claim 18, wherein said two tool components are held captive by complementary threaded sections on said first and second tool components.

20. The set of components of claim 18, wherein said first tool component includes an exterior surface that is shaped to receive a wrench-like tool to hold said first tool component and said carrier device non-rotationally.

21. The set of components of claim 16, wherein said coupling means includes a component that is separate from said carrier.

22. The set of components of claim 16, wherein said coupling means includes a resilient structure.

23. The set of components of claim 16, wherein said resilient structure is an O-ring that partially resides within said through-bore of said carrier device.

24. A set of components for delivering an implant to a site at which said implant is to be installed in living jawbone and taking an impression of said site with impression material, said implant having a gingival end with a manipulating fitting and a threaded bore extending inwardly from said gingival end, said set comprising:

a carrier device having an upper end, a lower end, a through-bore extending between said lower and upper ends, and a fitting for mating with said manipulating fitting of said implant, said through-bore in the region adjacent to said upper end including a rigid non-circular socket;

an implant screw attaching said carrier device to said implant, said implant screw having a lower threaded portion for engaging said threaded bore of said implant and a head for stopping on a shoulder within said through-bore of said carrier device;

an impression coping for taking an impression of said site in the mouth, said impression coping includes means for mating with said carrier device and means for indexing said impression coping within said impression material, said carrier device and said impression coping being used in conjunction with said impression material to develop a prosthetic tooth for said site; and means for securing said impression coping to said carrier device.

25. The set of components of claim 24, wherein said mating means of said impression coping includes a rigid non-circular protrusion for mating with said rigid non-circular socket of carrier device.

26. The set of components of claim 25, wherein said securing means includes a long screw that expands said non-circular protrusion into tight engagement within said non-circular socket.

27. The set of components of claim 24, wherein said impression coping is a pick-up type of impression coping that remains within said impression material when said impression material is removed from said site.

28. The set of components of claim 24, wherein said impression coping is a transfer type of impression coping that remains attached to said carrier device when said impression material is removed from said site and said transfer-type of impression coping is later reinserted into said impression material.

29. A set of components for delivering an implant to a site in living jawbone and installing said implant at said site, said implant having a gingival end with a manipulating fitting and a threaded bore extending inwardly from said gingival end, said set comprising:

a carrier device having an upper end, a lower end, a through-bore extending between said lower and upper ends, and a fitting for mating with said manipulating fitting of said implant, said through-bore in the region adjacent to said upper end including a non-circular socket, said carrier including a resilient structure;

an implant screw attaching said carrier device to said implant, said implant screw having a lower threaded portion for engaging said threaded bore of said implant and a head for stopping on a shoulder within said through-bore of said carrier device; and an implant-insertion tool for imparting rotational movement to said carrier device and said implant, said implant-insertion tool engaging said non-circular socket of said carrier device and said resilient structure to retain said implant-insertion tool within said non-circular socket.

30. The set of components of claim 29, further including at least one other implant-insertion tool, each implant-insertion tool having a lower end portion fitting within said non-circular socket and an upper end portion having means for connecting said implant-insertion tool to a rotational machine, wherein one of said implant-insertion tools has a length that is different than the length of the other one of tools.

31. The set of components of claim 29, wherein said implant-insertion tool includes a ball-hex configuration that mates with said non-circular socket.

32. The set of components of claim 29, wherein said implant-insertion tool has an end to be engaged by a clinician for manually inserting said implant into said jawbone.

33. The set of components of claim 25, wherein said resilient structure includes a rubber structure adjacent to said non-circular socket.

34. A method of taking an impression during first-stage surgery immediately after an implant is installed into a site within living jawbone, said method comprising the steps of:

providing a package containing said implant attached to a carrier;

opening said package;

transporting said implant and said attached carrier to said site;

installing said implant into its final position within said jawbone by engaging said carrier with a tool imparting rotational movement to said carrier and said implant;

affixing an impression coping to said carrier;

taking an impression of said site with impression material that is placed around said impression coping and said carrier;

removing said impression coping from said carrier; and releasing said carrier from said implant.

35. The method of claim 34, wherein said implant is attached to said carrier by an implant screw, and said step of releasing said carrier includes the steps of threadably releasing said implant screw from said implant simultaneously with holding said carrier and said implant non-rotationally.

36. The method of claim 34, wherein said impression coping is a pick-up type of impression coping, said step of removing said impression coping from said carrier being accomplished by a step of removing said impression material from said site.

37. The method of claim 34, wherein said impression coping is a transfer type of impression coping, said step of affixing said impression coping to said carrier including installing a fastener that attaches said impression coping to said carrier, and said step of removing said impression coping from said carrier including the steps of releasing said fastener.

38. The method of claim 37, wherein said step of installing said fastener includes expanding a portion of said impression coping into tight engagement with said carrier.

39. The method of claim 34, further including the step of creating a model of said site with said impression material.

40. The method of claim 39, wherein said step of creating said model includes the steps of attaching said carrier to an implant analog and reaffixing said impression coping to said carrier.

41. A set of components for delivering an implant to a site in living jawbone at which said implant is to be installed, said implant having a gingival end with a manipulating fitting and a threaded bore extending inwardly from said gingival end, said set comprising:
   a carrier device having an upper end, a lower end, a through-bore extending between said lower and upper ends, and a fitting for mating with said manipulating fitting of said implant, said through-bore in the region adjacent to said upper end including a non-circular socket for receiving an implant-insertion tool imparting movement to said carrier device and said implant, said carrier device further includes means for retaining said implant-insertion tool in said non-circular socket wherein said retaining means includes an irregularity within said non-circular socket; and
   an implant screw for attaching said carrier device to said implant, said implant screw having a lower threaded portion for engaging said threaded bore of said implant and a head for stopping on a shoulder within said through-bore of said carrier device.

42. The set of components of claim 41, wherein said irregularity includes a rubber structure adjacent to said non-circular socket in said through-bore.

43. A set of components for delivering an implant to a site in living jawbone at which said implant is to be installed, said implant having a gingival end with a manipulating fitting and a threaded bore extending inwardly from said gingival end, said set comprising:
   a carrier device including an internal surface defining a through-bore extending therethrough and a fitting for mating with said manipulating fitting of said implant, said carrier device including a tool-retaining structure including an irregularity within said through-bore;
   an implant screw for attaching said carrier device to said implant, said implant screw having a lower threaded portion for engaging said threaded bore of said implant; and
   a tool for releasing said implant screw from said implant so as to detach said carrier device from said implant, said tool including means for imparting rotation to said implant screw, said tool engaging said tool-retaining structure to maintain connection of said carrier device to said implant when said carrier device is detached from said implant.

44. The set of components of claim 43, wherein said irregularity is located in said through-bore.

45. The set of components of claim 44, wherein said irregularity is a rubber structure.

46. The set of components of claim 43, wherein said irregularity is a rubber structure.

47. A set of components for delivering an implant to a site in living jawbone at which said implant is to be installed, said implant having a gingival end with a manipulating fitting and a threaded bore extending inwardly from said gingival end, said set comprising:
   a carrier device having an upper end, a lower end, a through-bore extending between said lower and upper ends, and a fitting for mating with said manipulating fitting of said implant, said through-bore in the region adjacent to said upper end including a non-circular socket;
   an implant screw for attaching said carrier device to said implant, said implant screw having a lower threaded portion for engaging said threaded bore of said implant and a head for stopping on a shoulder within said through-bore of said carrier device; and
   an implant-releasing tool for releasing said implant screw from said implant so as to detach said carrier device from said implant, said implant-releasing tool including means for prohibiting the rotation of said carrier device and means for imparting rotation to said implant screw, said rotational prohibiting means non-rotationally holding said carrier device while said implant screw is threadably released from said threaded bore of said implant; and
   wherein said implant-releasing tool includes two tool components, a first tool component includes said rotational prohibiting means and a second tool component includes rotational imparting means, said first tool component includes an exterior surface that is shaped to receive a wrench-like tool to hold said first tool component and said carrier device non-rotationally.

* * * * *

UNITED STATES PATENT AND TRADEMARK OFFICE
CERTIFICATE OF CORRECTION

PATENT NO : 5,964,591
DATED : October 12, 1999
INVENTOR(S): Beaty et al.

It is certified that error appears in the above-identified patent and that said Letters Patent is hereby corrected as shown below:

Column 16, line 6: Replace "implant" with --tool--.

Column 16, line 9: Replace "irregularity" with --tool-retaining structure--.

Signed and Sealed this

Thirteenth Day of March, 2001

*Attest:*

NICHOLAS P. GODICI

*Attesting Officer*     *Acting Director of the United States Patent and Trademark Office*